US011183293B2

(12) United States Patent
Lu et al.

(10) Patent No.: US 11,183,293 B2
(45) Date of Patent: Nov. 23, 2021

(54) OPTIMIZED ANATOMICAL STRUCTURE OF INTEREST LABELLING

(71) Applicant: KONINKLIJKE PHILIPS N.V., Eindhoven (NL)

(72) Inventors: Kongkuo Lu, Briarcliff Manor, NY (US); Alexandra Groth, Hamburg (DE); Yuechen Qian, Lexington, MA (US); Axel Saalbach, Hamburg (DE); Ranjith Naveen Tellis, Cambridge, MA (US); Daniel Bystrov, Hamburg (DE); Ran Cohen, Haifa (IL); Bela Fadida, Haifa (IL); Lior Wolloch, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 499 days.

(21) Appl. No.: 15/524,322

(22) PCT Filed: Oct. 22, 2015

(86) PCT No.: PCT/IB2015/058144
§ 371 (c)(1),
(2) Date: May 4, 2017

(87) PCT Pub. No.: WO2016/071791
PCT Pub. Date: May 12, 2016

(65) Prior Publication Data
US 2017/0372007 A1    Dec. 28, 2017

Related U.S. Application Data

(60) Provisional application No. 62/076,508, filed on Nov. 7, 2014.

(51) Int. Cl.
*G16H 30/20* (2018.01)
*G06F 16/58* (2019.01)
(Continued)

(52) U.S. Cl.
CPC ......... *G16H 30/20* (2018.01); *G06F 16/5866* (2019.01); *G06F 40/30* (2020.01);
(Continued)

(58) Field of Classification Search
CPC ............... G06F 19/321; G06F 16/5866; G06F 17/2785; G06K 9/4676; G06K 9/66
(Continued)

(56) References Cited

U.S. PATENT DOCUMENTS 7,792,778 B2    9/2010    Zhou et al.
8,229,881 B2    7/2012    Pedro et al.
(Continued)

FOREIGN PATENT DOCUMENTS

JP    2009193539    8/2009
JP    2010003135    1/2010
(Continued)

OTHER PUBLICATIONS

Sinha, U. et al., "Image Study Summarization of Mr. Brain Images by Automated Localization of Relevant Structures", Annals of the New York Academy of Sciences, New York Academy of Sciences, U.S., vol. 980, No. 1, Dec. 1, 2002, pp. 278-286.
(Continued)

*Primary Examiner* — Jason S Tiedeman
*Assistant Examiner* — Rachel F Durnin

(57) ABSTRACT

A system (100) for detecting and labeling structures of interest includes a current patient study database (102) containing a current patient study (200) with clinical contextual information (706), a statistical model patient report database (104) containing at least one or more prior patient documents containing clinical contextual information (706), an image metadata processing engine (118) configured to extract metadata for preparing an input for an anatomical structure classifier (608), a natural language processing
(Continued)

engine (120) configured to extract clinical context information (706) from the prior patient documents, an anatomical structure detection and labeling engine (718) or processor (112), and a display device (108) configured to display findings from the current patient study. The anatomical structure detection and labeling engine (718) or processor (112) is configured to identify and label one or more structures of interest (716) from the extracted metadata and clinical context information (706) and aggregate series level data.

9 Claims, 9 Drawing Sheets

(51) Int. Cl.
  G06F 40/30     (2020.01)
  G16H 70/60     (2018.01)
  G06K 9/46      (2006.01)
  G06K 9/66      (2006.01)
(52) U.S. Cl.
  CPC ............ *G06K 9/4676* (2013.01); *G06K 9/66* (2013.01); *G16H 70/60* (2018.01)
(58) Field of Classification Search
  USPC .......................................... 705/2–3
  See application file for complete search history.

(56) References Cited

U.S. PATENT DOCUMENTS

| | | | |
|---|---|---|---|
| 8,369,585 B2 * | 2/2013 | Graessner | G06K 9/00 382/115 |
| 8,369,593 B2 | 2/2013 | Peng et al. | |
| 8,494,238 B2 | 7/2013 | Zhou | |
| 8,572,086 B2 | 10/2013 | Soderberg et al. | |
| 8,588,519 B2 | 11/2013 | Liu et al. | |
| 8,625,866 B2 | 1/2014 | Hill et al. | |
| 8,625,869 B2 | 1/2014 | Harder et al. | |
| 8,953,858 B2 | 2/2015 | Becker et al. | |
| 9,081,877 B2 | 7/2015 | Futami | |
| 2007/0238948 A1 * | 10/2007 | Bartsch | G06T 7/0012 600/407 |
| 2008/0027889 A1 * | 1/2008 | Zhou | G06F 19/00 706/50 |
| 2008/0150937 A1 * | 6/2008 | Lundstrom | G06T 15/005 345/419 |
| 2009/0020638 A1 | 1/2009 | Becker et al. | |
| 2009/0028403 A1 * | 1/2009 | Bar-Aviv | G16H 50/20 382/128 |
| 2009/0080731 A1 | 3/2009 | Krishnapuram et al. | |
| 2009/0290802 A1 | 11/2009 | Xian-Sheng et al. | |
| 2010/0172567 A1 * | 7/2010 | Prokoski | A61B 5/0064 382/132 |
| 2011/0199390 A1 | 8/2011 | Iisuka | |
| 2012/0041779 A1 * | 2/2012 | Boroczky | G16H 50/20 705/2 |
| 2012/0283546 A1 * | 11/2012 | Zuehlsdorff | A61B 5/055 600/410 |
| 2013/0129165 A1 | 5/2013 | Dekel et al. | |
| 2013/0336553 A1 * | 12/2013 | Buisseret | G06T 7/13 382/128 |
| 2014/0003737 A1 | 1/2014 | Fedorovskaya et al. | |
| 2014/0180721 A1 | 6/2014 | Cheline et al. | |
| 2015/0193583 A1 * | 7/2015 | McNair | G16H 50/20 705/2 |

FOREIGN PATENT DOCUMENTS

| | | |
|---|---|---|
| JP | 2013182444 | 9/2013 |
| JP | 2014059892 | 4/2014 |

OTHER PUBLICATIONS

Sinha, U. et al., "A Review of Medical Imaging Informatics", Annals of the New York Academy of Sciences, New York Academy of Sciences, U.S., vol. 980, No. 1, Jan. 1, 2002, pp. 168-197.

Sinha, U et al., "Structure Localization in Brain Images: Application to Relevant, Image Selection", Symposium, American Medical Informatics Association, Nov. 3, 2001, pp. 622-626.

Tommasi, T et al., "Discriminative cue integration for medical image annotation", DOI:10.1016/j.patrec.2008.03.009.

* cited by examiner

| Anatomical region | # of studies | Likelihood to be diagnosed |
|---|---|---|
| lungs and pleura | 27 | 93.10% |
| mediastinum and hila | 23 | 79.31% |
| bowel, mesentery | 20 | 68.97% |
| abdomen | 19 | 65.52% |
| chest wall | 19 | 65.52% |
| kidneys, ureters | 16 | 55.17% |
| liver, biliary tract | 11 | 37.93% |
| retroperitoneum, lymph nodes | 9 | 31.03% |
| adrenal glands | 6 | 20.69% |
| spleen | 4 | 13.79% |
| bones, soft tissues | 4 | 13.79% |
| pancreas | 2 | 6.90% |
| bladder | 2 | 6.90% |
| upper abdomen | 2 | 6.90% |
| lymph nodes | 2 | 6.90% |
| uterus, adnexa | 1 | 3.45% |
| lung apices | 1 | 3.45% |

| Anatomical structure | Likelihood to be diagnosed |
|---|---|
| lungs and pleura | |
| mediastinum and hila | 85.19% |
| bowel, mesentery | 74.07% |
| abdomen | 70.37% |
| chest wall | 70.37% |
| kidneys, ureters | 59.26% |
| liver, biliary tract | 40.74% |
| retroperitoneum, lymph nodes | 33.33% |
| adrenal glands | 22.22% |
| spleen | 14.81% |
| Other... | |

| Anatomical structure | Likelihood to be diagnosed |
|---|---|
| lungs and pleura | |
| mediastinum and hila | 85.19% |
| bowel, mesentery | 74.07% |
| abdomen | 70.37% |
| chest wall | 70.37% |
| kidneys, ureters | 59.26% |
| liver, biliary tract | 40.74% |
| retroperitoneum, lymph nodes | 33.33% |
| adrenal glands | 22.22% |
| spleen | 14.81% |
| Other... | |

OPTIMIZED ANATOMICAL STRUCTURE OF INTEREST LABELLING

CROSS-REFERENCE TO PRIOR APPLICATIONS

This application is the U.S. National Phase application under 35 U.S.C. § 371 of International Application No. PCT/IB2015/058144, filed on Oct. 22, 2015, which claims the benefit of U.S. Provisional Application No. 62/076,508, filed on Nov. 7, 2014. These applications are hereby incorporated by reference herein.

The present application relates generally to detecting and visualizing pertinent patient information and finding-specific suggestions in radiology workflow. It finds particular application in conjunction with providing finding-specific suggestions to a radiologist of relevant anatomical structures to review in a patient based upon information extracted from non-image data such as prior patient reports and DICOM information and will be described with particular reference there. It also finds particular application in conjunction with providing these finding-specific suggestions to a radiologist based upon priority for a radiologist to review and will be described with particular reference thereto. However, it is to be understood that it also finds application in other usage scenarios and is not necessarily limited to the aforementioned application.

It has been recognized that quantitative imaging helps detect diseases in an early stage, improve diagnosis accuracy and consistency, suggest advanced treatment plan and guidance, and enable efficient patient follow up. However, a very low percentage of studies were actually processed and diagnosed using advanced visualization and quantitative imaging systems. Efforts have been made to contribute to the development of image visualization and processing tools. However it is quite challenging, and often cumbersome, for clinicians to take full advantage of the imaging systems, without comprehensive training and consistent support. Detecting existing organs, or key anatomical structures from a patient image is quite challenging without prior knowledge of the patient and prioritized structures to be diagnosed. On one hand, a segmentation technique may be object dependent while on the other hand, it is unknown which structures are expected, thus a global optimization is used and the process is time consuming.

In a typical radiology interpretation work flow, given the reason for the scan and other prior knowledge of the patient, the radiologist usually needs to identify and annotate a relevant finding. The radiologist annotates a finding and then scans through the rest of the images to look for other findings or related findings. The task could be quite stressful due to the limited time for an individual image and high volume of the patients to be investigated by a physician. Current systems do not guide the radiologist to review other anatomical structures in a patient based upon a priority. This can lead to missed findings and/or make it time consuming to detect the findings.

Additionally, due to improvements in medical imaging, the size of image data has significantly increased over the years (e.g. as a result of a higher image resolution/the use of multi-temporal or multimodal data). Hence, the data retrieval process (from the image storage e.g. PACS to the workstation) takes a non-negligible time in the workflow of the radiologist waiting to inspect the data. This is even more prevalent when a hospital or other medical facility uses cloud-based services where data has to be transferred from a remote server.

During review, a radiologist not only reviews the anatomical structures in question but also wants to review related anatomical structures. This means that for diagnosing a certain disease, the radiologist has a focus on specific anatomical regions, and expects the data displayed in a suitable manner (e.g. with respect to the field of view and image orientation). Although the data loading process cannot be accelerated, the efficiency of the workflow itself can be improved, by transferring and displaying the most important data first. Consider a situation where a radiologist has to inspect a CT scan of a cardiac patient while the last available data set in the PACS system is a chest/abdominal scan. The present application seeks to improve the transfer of this image data. The system reviews the images and optimizes the data transfer based on the clinical needs. Once the images of the most relevant anatomical structures are transmitted, the remaining data would be transferred in a streaming like fashion.

The present application provides a system and method which retrieves a patient's medical data record and, using information extracted from these reports combined with the extracted DICOM data, provides a radiologist with the most likely affected, or high-risk, anatomical structures of interest (SOI). These SOIs are first segmented and then given to the radiologist for review. The system also uses the information extracted from the patient reports and the DICOM tags to generate a probability model. The probability model presents the radiologist with additional anatomical structures that should be reviewed based upon the current findings, the reason for examination, and past historical data from other patients. These additional anatomical structures for review are areas that are most likely to also be affected based upon the given information. The present application further provides utilizing a workflow-driven data transmission scheme to optimize transmission of image data to the physician. Using the context information given by the current workflow, selected image areas/anatomical regions with the highest probability of being relevant to the examination are transmitted first. The remaining segments/anatomical regions are given lower priority and are transmitted to the radiologist last.

The present application also provides new and improved methods and systems which overcome the above-referenced problems and others.

In accordance with one aspect, a system for detecting and segmenting structures of interest is provided. The system includes a current patient study database, a statistical model patient report database, an image metadata processing engine, a natural language processing engine, an anatomical structure detection and labeling engine, a display device, and one or more processors. The one or more processors are configured to prepare a list of suggested anatomical structures from the anatomical structure classifier and form a prioritized list of structures of interest, process the prioritized list of structures of interest through the anatomical structure detection and labeling engine to form an optimized structure of interest list for the current patient study, apply the optimized structure of interest list from the current study to the volumetric image to detect and label structures of interest, and control the display device to display the optimized structures of interest.

In accordance with another aspect, a method for optimizing detecting and labeling structures of interest is provided. The method extracts clinical contextual information and DICOM metadata from a current patient study and at least one prior patient documents, performs statistical analysis on the extracted clinical contextual information, and employ anatomical structure classifier based on the DICOM data to generate a list of suggested anatomical structures in the current patient study. The method also extracts anatomical structures from the current patient study to create a patient high risk analysis report and then detects and labels the anatomical structure. The processors combine the suggested anatomical structures and the high risk anatomical structures to form an optimized prioritized list of structures of interest. The list is optimized and added to the volumetric image and then displayed to the physician.

One advantage resides in improved determination of the most probable anatomical structures of interest using known patient medical information and DICOM tags.

Another advantage resides in optimized transmission of image data.

Another advantage resides in improved clinical workflow.

Another advantage resides in improved patient care.

Still further advantages of the present invention will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 9 illustrates an association among anatomical structures showing the likelihood of other anatomical structures to be diagnosed in the same study when it is known there is a positive finding in another anatomical structure.

Anatomical regions in medical images are identifiable using a variety of image processing techniques, including classification based anatomy detection, registration using statistical templates and model-based segmentation or a combination of those techniques. One possible embodiment is a sliding window approach. In this context, anatomy detection is a classification task. Using a feature based representation of a set of positive and negative image patches machine learning is used to discriminate between the two classes. In the detection phase the classified image is used in order to identify image regions with a high probability for the target anatomy. Using this approach, a large number of detectors might have to be applied to the image in order to estimate the probabilities for all anatomies under consideration. Furthermore, the selection of suitable acceptance thresholds for the probabilities is critical to balance the trade-off between false positive and false negative detections. To this end, supplemental information such as organ probabilities estimates from DICOM metadata or a report is used for the selection of the classified or for weighing of the outcome.

The present application is directed to a system and method for automatically detecting and segmenting related anatomical structures based upon a patient's prior medical history, current medical issues, and related information from a prediction table. Additionally, DICOM tags are used to improve the relevant information being presented to a treating physician. The present application is inspired by the insight that a patient's prior medical history combined known information from other patients and DICOM tags can improve the likelihood that a treating physician will examine not only the area of immediate complaint but also review related areas that may also be afflicted with the same or similar illness. For example, if the patient has a finding in the lung, the system determines all such other patients having a finding in the lung and presents to the radiologist other anatomical areas that are most likely affected.

Specifically, a radiologist reviews patient data from the system. The patient data is comprised of clinical context data and DICOM data. The clinical context data comprises information such as the reason for the visit or referral letter, prior reports, and any clinical indications or annotations, etc. With respect to the clinical context data, the reports contain both information of the individual patient and information about a select population. Since all the statements included in the report were confirmed by physicians, the extracted information is considered reliable.

Figure 1:
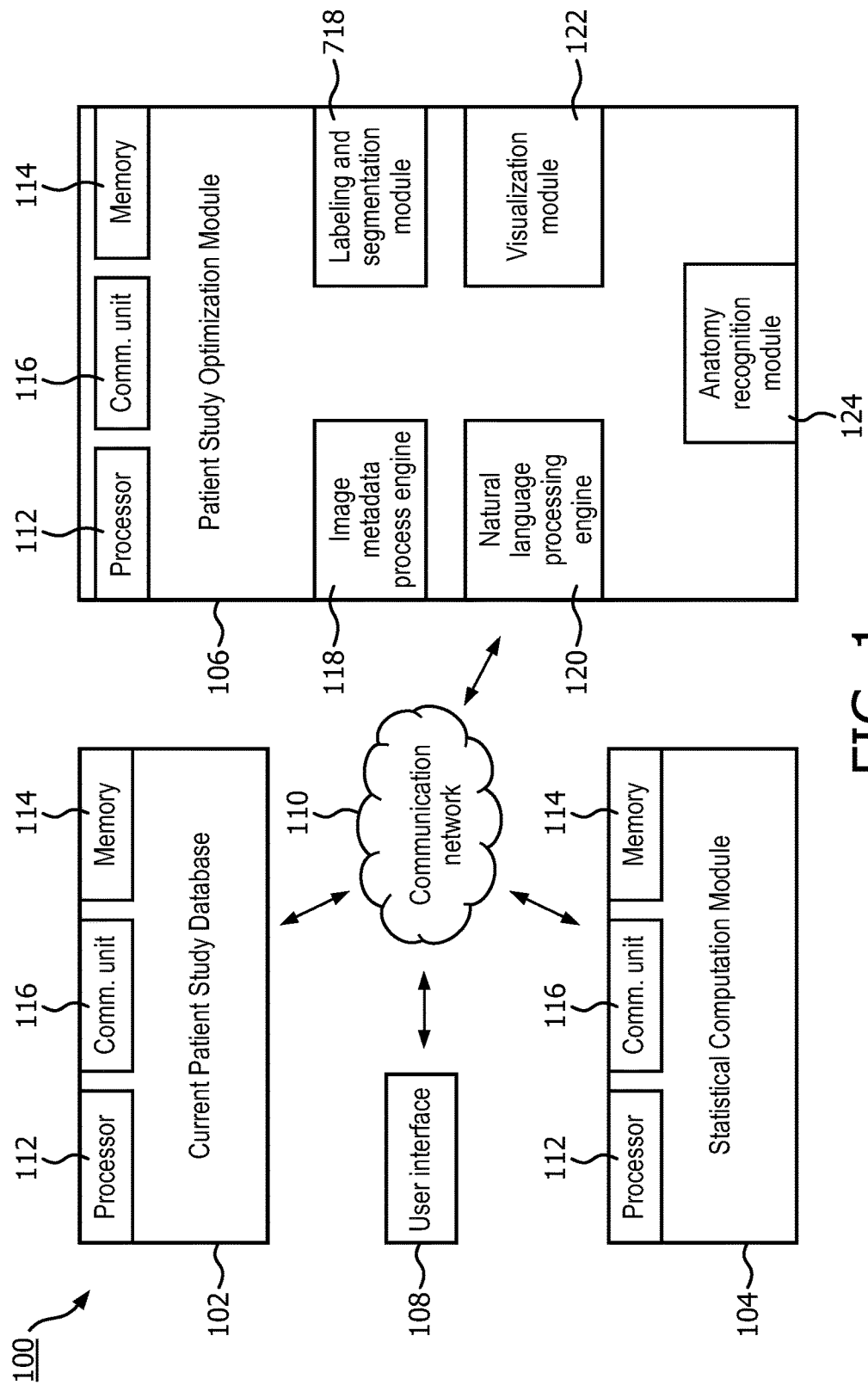
FIG. 1 illustrates a block diagram showing a representative system for collecting the patient data and communicating the results to the physician.

With reference to FIG. 1, a block diagram illustrating a representative system for optimizing clinical reports and presenting the information to a physician is shown. The system 100 suitably includes a current Patient Study Database 102, a Statistical Computation Module 104, a Patient Study Optimization Module 106, a user interface 108, interconnected via a communications network 110. It is contemplated that the communications network 110 includes one or more of the Internet, Intranet, a local area network, a wide area network, a wireless network, a wired network, a cellular network, a data bus, and the like. It should also be appreciated that the components of the system be located at a central location or at multiple remote locations.

The components of the system 100 suitably include one or more processors 112 executing computer executable instructions embodying the foregoing functionality, where the computer executable instructions are stored on memories 114 associated with the processors 112. It is, however, contemplated that at least some of the foregoing functionality is implemented in hardware without the use of processors. For example, analog circuitry can be employed. Further, the components of the system 100 include communication units 116 providing the processors 112 an interface from which to communicate over the communications network 110 and provide the information to the physician over the user interface 108. The Patient Study Optimization Module 106 includes an Image Metadata Process engine 118, a Labeling and Segmentation Module 718, a natural language processing engine 120, and a visualization module 122, all further described in FIG. 7. The Patient Study Optimization module also contains an anatomy recognition module 124. This module 124 receives the clinical context information from the current and prior patient reports and indexes the information by anatomical structure of interest and location for future use and reference in a lookup table. Even more, although the foregoing components of the system 100 were discretely described, it is to be appreciated that the components can be combined.

In one embodiment, a patient report is received from a current patient study database(s) (PACS, HIS, RIS, etc.) 102 which contain the patient data reports and images and at least one prior patient document is retrieved from the statistical computation module 104. The document received from the statistical computation module 104 contains clinical contextual information. The current patient report and the prior patients' reports are received by the patient study optimization module 106. The documents are reviewed, and labeled with areas where findings have been observed. Based upon the diagnosed findings, the reports are also used to generate a list of high risk anatomical structures. An anatomical structure is labeled high risk if, based upon the information received from the prior patient reports, there is a higher likelihood that based upon the areas with a finding, other anatomical structures are also likely to have a finding. For example, in lung cancer studies, if it is known that there is a finding in the lung or the pleura, then there is also an 85% chance that there will be a finding in the mediastinum and hila. The mediastinum and hila are marked as high risk areas and are reviewed by the radiologist first to determine a diagnosis. To fully determine this association, as described above, the patient study optimization module 106 generates tables as later described in FIG. 4 and an association will be generated as described in FIG. 5.

Figure 2:
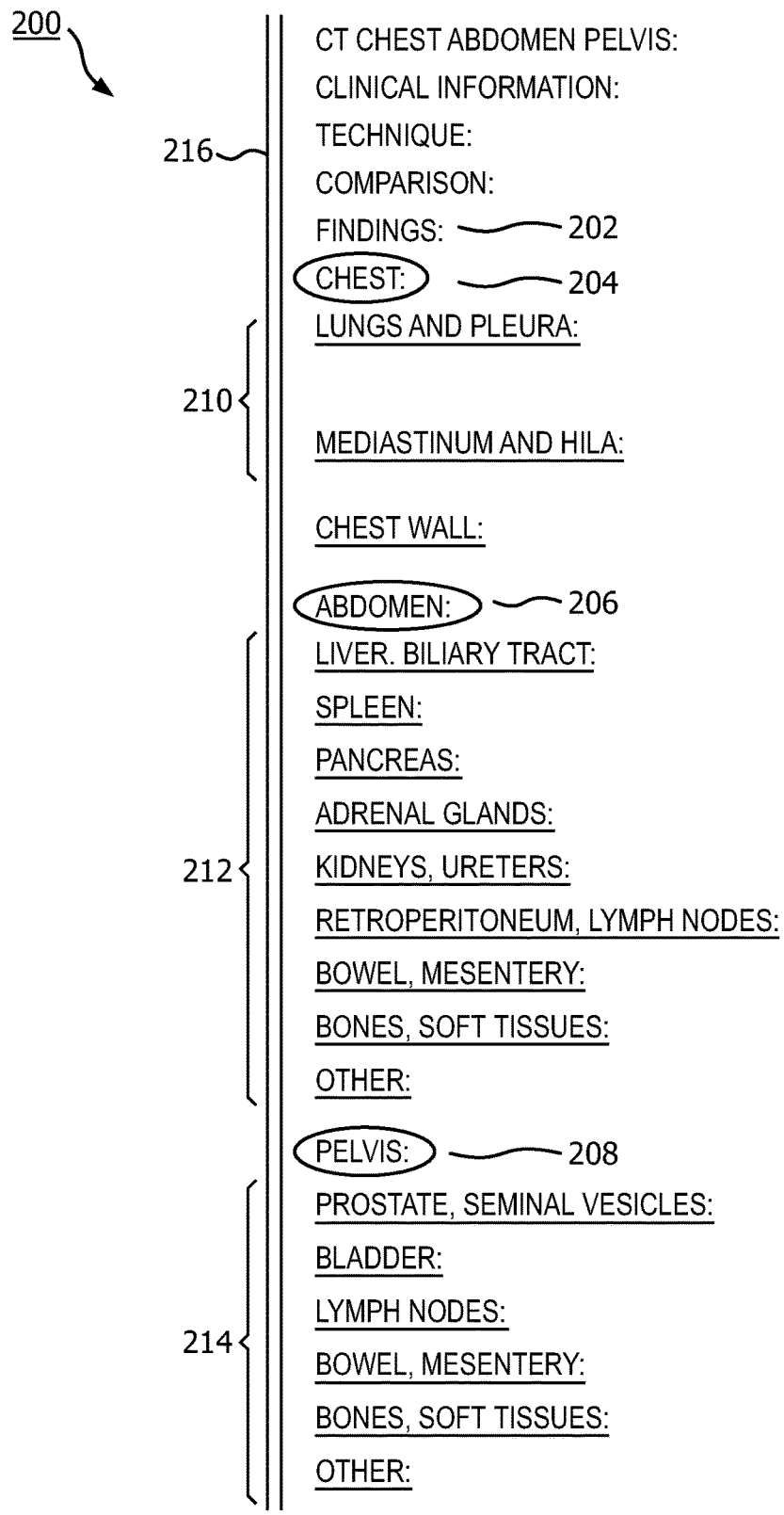
FIG. 2 illustrates an example patient report for use in an optimized anatomical structure of interest labeling preprocess for use in diagnostic workflow according to aspects of the present application.

With respect to FIG. 2, a patient clinical report is shown 200, for example, a radiology report. The report contains a FINDINGS section 202 that includes various body parts 204, 206, 208 and their associated anatomical regions 210, 212, 214. For each anatomical region 210, 212, 214, there is an associated statement indicating whether there has been a finding and indicates the measurement of the finding, if available. The clinical information section 216 of this report includes the reason for the study and related patient history.

Figure 3:
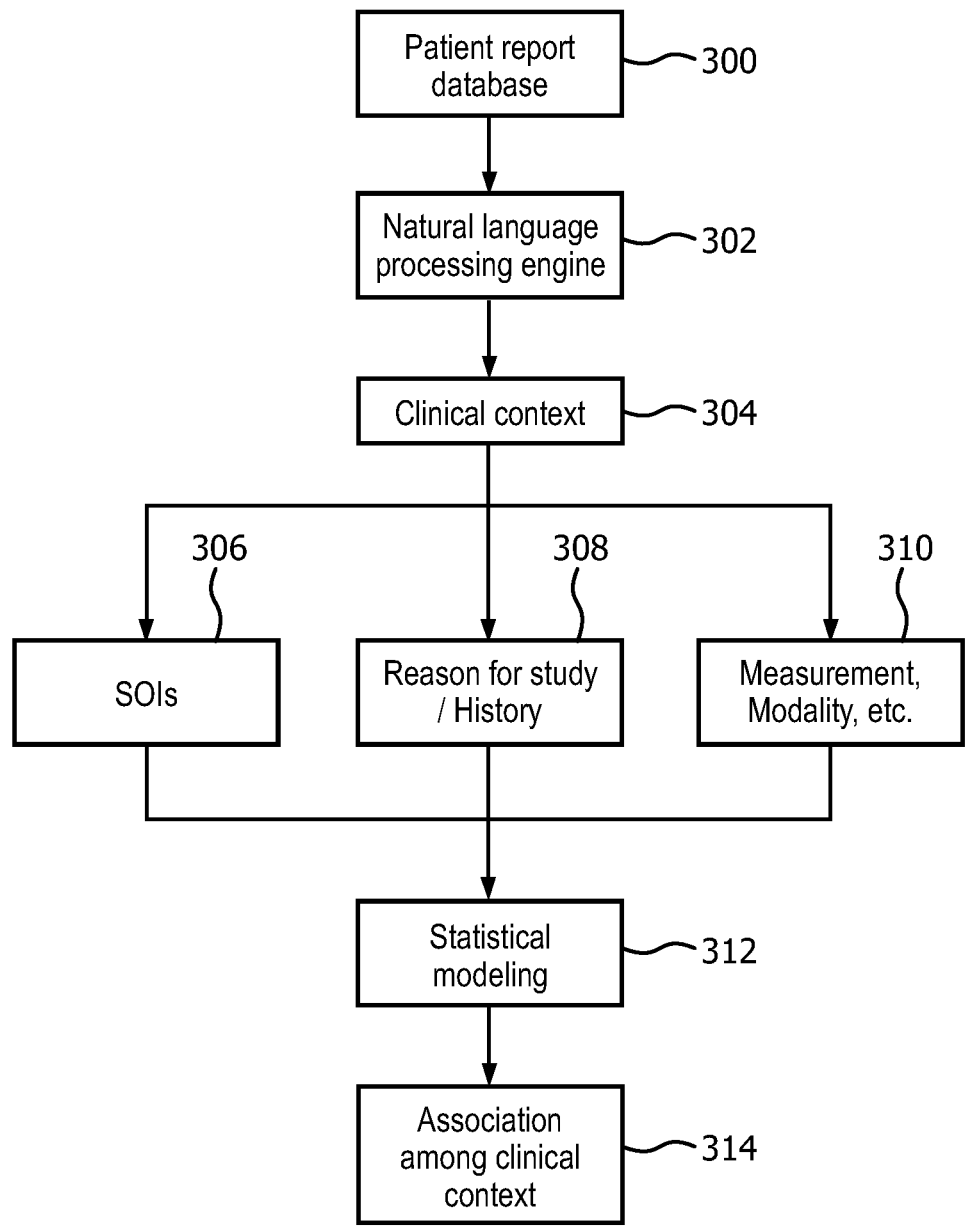
FIG. 3 illustrates a flowchart of the report processing module according to aspects of the present application.
Figure 4:
FIG. 4 illustrates a statistical summary chart of the most likely infected anatomical structures based upon information extracted from a patient clinical report according to aspects of the present application.

With further reference to FIG. 3 and FIG. 4, a process flowchart diagramming optimized SOI detection and labeling using patient clinical reports and DICOM tags is shown. Over a period of time, an institution may have accumulated several patient reports like the one described in FIG. 2. A patient clinical document 100 from the patient report database 300 is sent to the natural language processing engine 302 for interpretation and extraction. The natural language processing (NLP) engine 302 extracts the clinical context information 304 and associated body parts listed in the patient clinical document 200. This information is used to create a database that summarizes the extracted information from the patient clinical reports including the SOI 306, the reason or the study and patient history 308, and any findings such as measurement or modality 310. Based on this information, a module is designed to determine and compute a statistic model 312 of the anatomical structure. The statistical modeling information is then associated with the clinical context information such as the reason for study, history and findings 314.

FIG. 4 shows an example statistical summary report 400 of the most likely infected anatomical structures for a lung cancer patient. If patient history information is also available, a similar table is created to show the most likely infected anatomical structures for the patient with a history of a specific disease and current symptoms or findings. If it is known that one anatomical structure is diagnosed, there is a higher probability that other anatomical structures will show symptoms and exhibit findings.

Figures 5, 6:
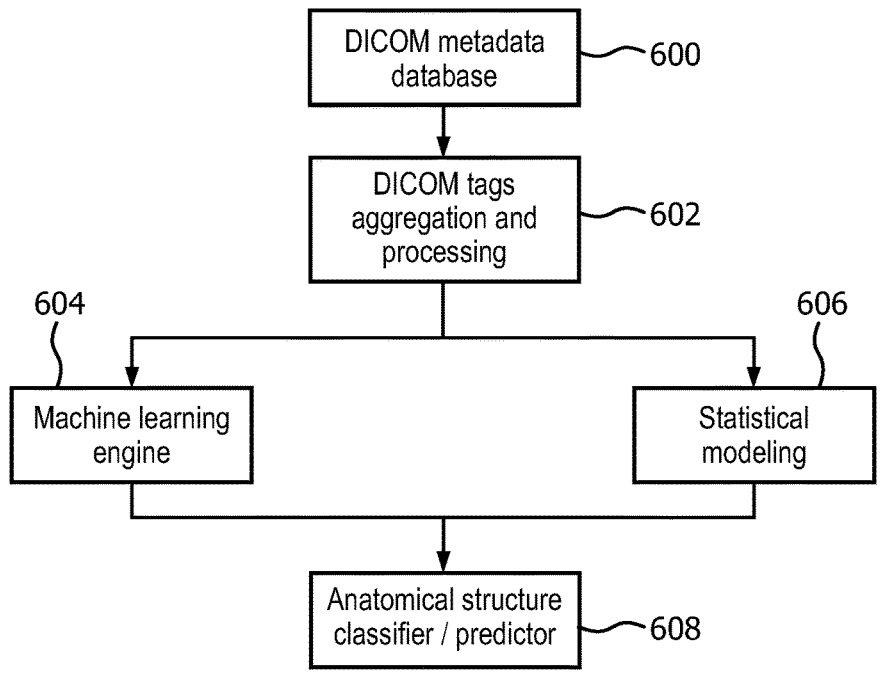
FIG. 5 illustrates a table indicating the likelihood of other anatomical structures being affected when it is known there is a positive finding in at least one anatomical finding of the patient according to aspects of the present application.
FIG. 6 illustrates a flowchart of the image metadata processing engine according to aspects of the present application.

With respect to FIG. 5 shows a probability chart 500 of other anatomical structures within a patient to be diagnosed when it is known that there is a positive finding in a first anatomical structure. For lung cancer studies, if there is a finding in the lungs and pleura, it is more likely that the mediastinum and hila also have findings that the physician knows to now look for.

With reference to FIG. 6, a flowchart illustrating the image metadata processing 600 module is shown. DICOM tags contain information relevant to anatomical structures existent in the current study such as: study description, protocol name, body part examined, series description, modality, contrast/bolus agent, etc. Some of these tags are study related tags while others are more specific to the series or volumetric image within the study. In order to obtain study related information, series level DICOM data is first aggregated together and then processed 602. After data segregation, Bag of Words (BoW) features are constructed out of all relevant free text tags. BoW is one approach to text processing. The final features consist of all selected tags and the BoW features. Using these BoW features, associated with statistical modeling information 606 identified by experts based on DICOM metadata and their experience, a machine learning engine 604 is configured to train a DICOM metadata based classified/predictor 608. This module receives DICOM metadata to represent various patient populations. The outcome is used as an initial anatomical structure detection.

Figure 7:
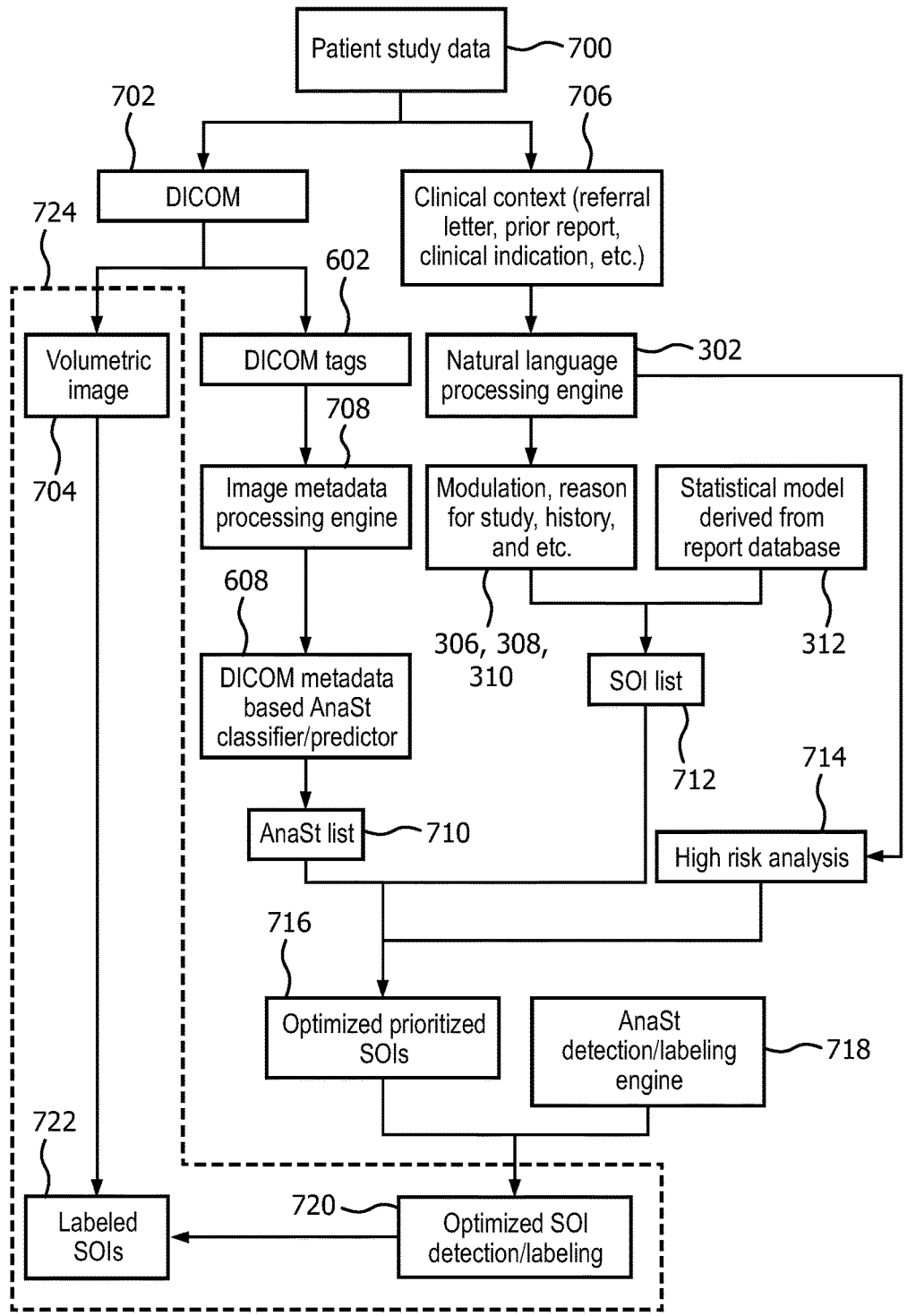
FIG. 7 illustrates a flowchart of SOI detection and labeling optimization according to aspects of the present invention.

With further reference to FIG. 7, a flowchart displaying the representative method for retrieving clinical context information and DICOM information for a patient study is shown. For a new study, the patient data 700 is first separated into DICOM data 702 including metadata 602, volumetric image data 704, and other clinical context data 706. The clinical context data 706 is passed to a natural language processing engine 202 to extract key statements including modality 310, reason for the study, clinical history and prior recommendations 308, SOIs 306 etc. The information is then combined with the statistical model derived from the report database 312 to form the SOI list 712. The remaining DICOM data 702 is divided into the volumetric image data 704 and the DICOM metadata 602. The DICOM tags are processed through an image metadata process engine 708 where the outcome of the anatomical structure classifier/predictor 608 described in FIG. 6 creates the anatomical structure list 710. A high risk analysis of the anatomical structures is conducted for the current patient based on the patient historical report analysis 714. A high risk analysis for the current patient report will return to the radiologist the SOIs that have the highest probability of also being affected or diagnosed with a finding. These areas are shown to the radiologist first for review. An anatomical structure is deemed high risk based upon the information received from prior patient reports. This information is analyzed and combined to form a statistical analysis look up table as shown in FIG. 9. The high risk analysis data is combined with the patient report output SOI list 712, and the anatomical structure list 710, provides a list of optimized and prioritized SOIs 716. The anatomical detection and labeling engine 718 is configured and the information is combined with the optimized and prioritized SOIs 616 resulting in an optimized SOI detection and labeling engine 720 for the current study. The optimized list is then applied to the volumetric labeled image data 722 to actually detect and label the SOIs from the current image. In one embodiment, the labeling engine 720 uses an automatic or semi-automatic segmentation routine to segment one or more SOIs. The segmented structures can be outlined with a line around the edge, colorized, and the like. The combination of 704, 720, 722 forms a visualization engine 724 which selects one or more image planes through the volume image to be displayed. In another embodiment, the images are transferred to the diagnostician based on a priority which allows the diagnostician to start reviewing the preferred image view first while the remaining data/images are transferred. Additionally, the labeling engine 720 can select one or more substructures within an image (such as a heart) to transfer to the diagnostician. The substructure is transferred first and then remaining nearby substructures and complete structures are transferred later.

Figure 8:
FIG. 8 illustrates a representative lookup table generates from the report database processing is shown according to aspects of the present application.

With reference to FIG. 8, a representative lookup table 800 generated from report database processing is shown. When a physician observes a finding on an image, the finding is typically measured and recorded in the corresponding report. The measurements are then associated with the body part shown in the look up table. As an institution accrues more of these reports, a natural language processing module extracts all the findings in the report and associates them with a body part to create a database. If multiple anatomical structures contain positive findings from one report, then this indicates an association between the anatomical structures which is seen in the lookup table. The associations determined in the lookup table allow a physician to more accurately diagnose and treat a patient in the future. The indicated associations between anatomical structures in prior patient reports is used to show the likelihood of other anatomical structures likely to be diagnosed in the same study when it is known there is a positive finding. With further reference to FIG. 9, with the inputs from the lookup table, the system calculates the statistical probability of a particular anatomical region being diagnosed when a finding is noted 900. For example, if a patient has a finding in the kidney, the system also determines other patients who had findings in their kidneys and retrieves findings found in other body parts.

Figure 10:
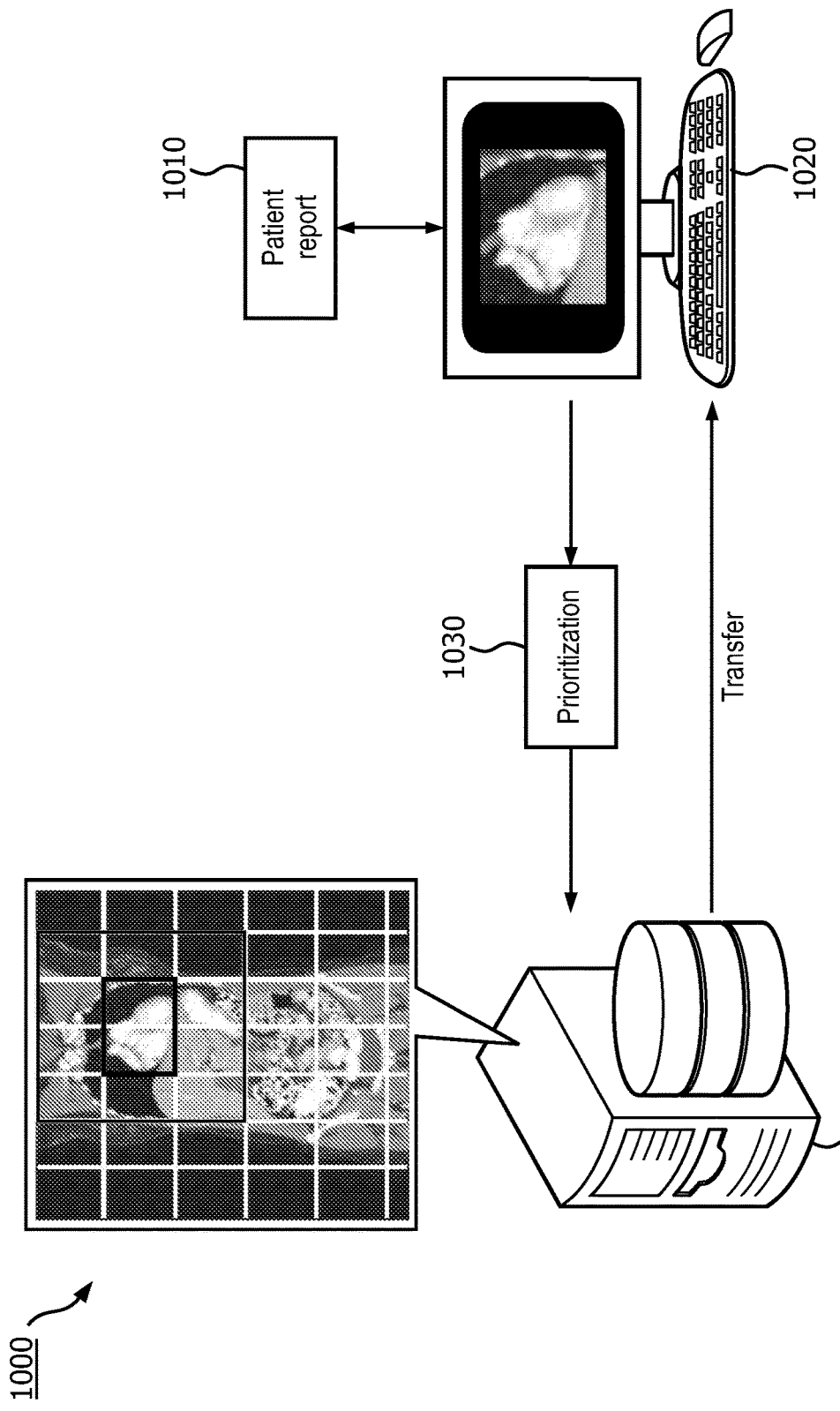
FIG. 10 illustrates a data transmission scheme where the most relevant anatomical structure is transmitted first.

With reference to FIG. 10, a system for retrieving and prioritizing patient clinical images based upon current and past patient history is illustrated. During a review of a patient file, a clinician will review all current and past images and notations to reach a diagnosis. There may be many patient images to review and the images may be large files. In an effort to streamline review, a clinician can review the higher priority images first taking into consideration the probability that certain anatomical structures will more likely be affected and images of the higher priority anatomical structures are transmitted to the clinician first. The clinician selects an image on from the patient report 1010 on the workstation 1020 to perform a prioritization 1030. The prioritization could be performed based on data from the radiology information system (RIS), hospital information system (HIS), previous user interaction, or based upon the lookup table described in FIG. 9. The system indexes the data in the database 1040 and a communications network 110 between the workstation 1020 and the patient clinical database 1040 allows relevant image data from the patient clinical database to be transferred to the clinician and displayed on the workstation 1020. In the alternative, regions of interest around a specific anatomical structure can be transferred based upon the above described prioritization.

As used herein, a processor includes one or more of a microprocessor, a microcontroller, a graphic processing unit (GPU), an application-specific integrated circuit (ASIC), a field-programmable gate array (FPGA), personal data assistant (PDA), cellular smartphones, mobile watches, computing glass, and similar body worn, implanted or carried mobile gear. It is further contemplated that as used herein, an engine can be formed using one or more processors configured to perform the task. As further used herein, a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system for guiding a radiologist through a radiology workflow by detecting and labeling anatomical structures of interest for review based on a priority, the system comprising:
   a display device;
   a current patient study database configured to store a current patient study including (i) DICOM data including metadata, at least one metadata tag, and volumetric image data of a volume image of a current patient including structures of interest of the current patient, and (ii) clinical context data concerning the structures of interest of the current patient;
   a statistical model patient report database configured to store a statistical model summarizing extracted information from prior patient reports including prior patient structures of interest, reasons for the study, prior patient history, and findings;
   one or more computer processors configured to:
      extract current patient clinical context information and associated body parts in the clinical context data from the current patient study database, the extracted current patient context information being combined with the statistical model from the statistical model patient report database to predict a current patient structures of interest list,
      extract the at least one metadata tag from the current patient study database and operate on the at least one metadata tag with an anatomical structure classifier from an anatomical structure database to generate an anatomical structure list, the anatomical structure list being combined with the predicted current patient structures of interest list to generate a prioritized predicted current patient structures of interest list,
      label the prioritized predicted current patient structures of interest from the prioritized predicted current patient structures of interest list in the volume image of the current patient,
      segment the labeled prioritized predicted current patient structures of interest in the volume image of the current patient based on an order of priority in the prioritized predicted current patient structures of interest list, and define image planes for the prioritized predicted, segmented current patient structures of interest through the volume image of the current patient, and control the display device to display the image planes of the predicted structures of interest of the current patient to the radiologist for review and annotation, wherein the image planes of the predicted current patient structures of interest having a higher priority of being affected are displayed before the image planes of the predicted current patient structures of interest having a lower priority of being affected.

2. The system according to claim 1, wherein the anatomical structure classifier is generated from metadata tags of prior patient studies using machine learning to train the anatomical structure classifier.

3. The system according to claim 1, wherein the one or more computer processors is further configured to:

conduct a risk analysis of the anatomical structures of the current patient based on the current patient clinical context data and identify high risk structures of the current patient, the generated high risk structures of the current patient being combined with the predicted structures of interest list and the anatomical structure list to generate the prioritized predicted current patient structures of interest list.

4. A system for guiding a radiologist through a radiological workflow by selecting, labeling, and displaying structures of potential interest to a radiologist for review and annotation, the system comprising:

one or more databases which store patient records including images, medical records, and diagnostic information about a patient to be diagnosed by a diagnostician and at least one other patient with a similar diagnosis;

a user interface including a user input device configured to receive inputs from the diagnostician requesting images to be displayed and a display device;

one or more processors configured to:
based on the medical records of the patient to be diagnosed, predict anatomical structures of the patient to be diagnosed to be displayed for diagnosis,
natural language process the medical records of the patient to be diagnosed,
use machine learning or statistical modeling to configure a statistical model based on natural language processed medical records of other patients,
from the natural language processed medical records, predict probabilities that other anatomical structures of the patient to be diagnosed are affected,
from the predicted anatomical structures of the patient to be diagnosed to be displayed and the predicted probabilities of the other anatomical structures of the patient to be diagnosed being affected, generate a prioritized list of anatomical structures of the patient to be diagnosed,
label and segment the other anatomical structures of the patient to be diagnosed in an order of the predicted probabilities of being affected,
define image planes for the labeled and segmented anatomical structures of the patient to be diagnosed, and
control the display device to display to the radiologist the image planes of the patient to be diagnosed which show the other anatomical structures of the patient to be diagnosed on the prioritized list on the display device in an order based on the prioritized list for review and annotation.

5. A method for guiding a radiologist through a radiology workflow by detecting, labeling, and displaying images of anatomical structures of interest of a current patient to be diagnosed in a prioritized order comprising:

using natural language processing, extracting current patient clinical context information and associated anatomical structures of the current patient to be diagnosed from a current patient study stored in a current patient study database configured to store the current patient study, the current patient study including (i) DICOM data including at least one metadata tag, (ii) volumetric image data, and (iii) clinical context data;

combining the extracted current patient context information with a statistical model from a statistical model database configured to store the statistical model, the statistical model summarizing extracted clinical context information from prior patient reports including potential structures of interest, reasons for the study, prior patient histories, and findings to generate a structures of interest list;

extracting at least one metadata tag from the current patient study and operating on the metadata tag with an anatomical structure classifier to generate an anatomical structure of interest list for the current patient;

combining the anatomical structure list for the current patient with the potential structures of interest list to generate a prioritized anatomical structures of interest list for the current patient;

labeling the potential structures of interest in the prioritized anatomical structures of interest list for the current patient;

segmenting the labeled potential structures of interest for the current patient in a volume image of the current patient to be diagnosed;

defining image planes for each segmented structure of interest for the current patient through the volume image of the current patient to be diagnosed;

displaying to the radiologist the image planes of the potential structures of interest of the current patient to be diagnosed with the image planes of the potential structures of interest of the current patient to be diagnosed with a higher priority being displayed before the image planes of the potential structures of interest of the current patient to be diagnosed having a lower priority.

6. A system for detecting, labeling, and displaying images of anatomical structures of interest comprising:

one or more processors configured to perform the method of claim 5;

one or more databases configured to store the current patient study, the statistical model, the anatomical structure classifier, and the labeled, segmented potential structures of interest of the current patient to be diagnosed; and a display device configured to display the image planes of the current patient to be diagnosed.

7. The method of claim 5, wherein the anatomical structure classifier is generated from metadata tags of prior patient studies using machine learning to train the anatomical structure classifier.

8. The method of claim 5, further including using the natural language processing to conduct a risk analysis of the anatomical structures of the current patient based on the current patient context information and identify high risk structures of the current patient, the generated high risk structures of the current patient being combined with the potential structures of interest list and the anatomical structure list to generate the prioritized anatomical structures of interest list for the current patient.

9. The method of claim 5, further including:
    annotating displayed image planes depicting affected anatomical structures.

\* \* \* \* \*